United States Patent [19]

Egan

[11] Patent Number: 5,417,700
[45] Date of Patent: May 23, 1995

[54] AUTOMATIC SUTURING AND LIGATING DEVICE

[75] Inventor: Thomas D. Egan, 12 South St., Marblehead, Mass. 01945

[73] Assignee: Thomas D. Egan, Marblehead, Mass.

[21] Appl. No.: 37,021

[22] Filed: Mar. 25, 1993

Related U.S. Application Data

[63] Continuation-in-part of Ser. No. 860,545, Mar. 30, 1992, abandoned.

[51] Int. Cl.$^6$ ............................................. A61B 17/04
[52] U.S. Cl. ...................................... 606/144; 606/27; 606/45; 606/103; 606/228
[58] Field of Search ................ 606/27, 30, 42, 45, 606/1, 103, 228, 187, 144–147

[56] References Cited

U.S. PATENT DOCUMENTS

| | | | |
|---|---|---|---|
| 1,822,330 | 9/1931 | Ainslie | 606/145 |
| 2,336,689 | 12/1943 | Karle | 606/147 |
| 3,513,848 | 5/1970 | Winston et al. | 606/228 |
| 3,608,095 | 3/1970 | Barry | 606/187 |
| 3,608,539 | 9/1971 | Miller | 606/187 |
| 4,050,100 | 9/1977 | Barry | 606/187 |
| 4,265,246 | 5/1981 | Barry | 606/187 |
| 4,312,337 | 1/1982 | Donohue | 606/103 |
| 4,369,787 | 1/1983 | Lasner et al. | 606/147 |
| 4,583,540 | 4/1986 | Malmin | 606/187 |
| 4,590,929 | 5/1986 | Klein | 606/103 |
| 4,635,638 | 1/1987 | Weintraub | 606/205 |
| 4,935,027 | 6/1990 | Yoon | 606/146 |
| 4,957,498 | 9/1990 | Caspri | 606/146 |

Primary Examiner—Gary Jackson
Attorney, Agent, or Firm—Jerry Cohen; Edwin H. Paul; Stephen Y. Chow

[57] ABSTRACT

A device and method of suturing closed an opening and ligating a vessel or duct comprising removable tissue puncturing means (22) or vessel surrounding means establishing a continuous channel (24) through said tissue or around said vessel from each side. A completed channel (24) is formed and suture material (26) is threaded through the channel making a complete loop. The thread is secured at an anvil (30) independent from said puncturing/surrounding means. The puncturing-/surrounding means is retracted leaving the thread, which is then tensioned closing the opening or occluding the vessel. The suture thread is secured and cut, forming a closed loop with overlapping ends. An energy transmitting device (38) melts the suture thread ends together forming a weld. The anvil (30) is removed leaving a knot-free completed stitch or ligature.

25 Claims, 12 Drawing Sheets

AUTOMATIC SUTURING AND LIGATING DEVICE

CROSS REFERENCE TO RELATED APPLICATIONS

This application is a continuation-in-part of my prior U.S. application Ser. No. 07/860,545, filed Mar. 30, 1992, now abandoned, and priority is hereby claimed under 35 USC 120 with respect to said prior application. The disclosure of said prior application is hereby incorporated by reference as though set out at length herein.

FIELD OF THE INVENTION

The present invention relates generally to closing or joining openings and wounds and tieing off of vessels and ducts in human and animal tissue and the like, and more particularly to suturing and ligating devices and methods for closing wounds and vessels, respectively, including hand held devices with specific application and utility in hard to reach and internal suturing and ligating needs.

BACKGROUND OF THE INVENTION

Suturing or closing of wounds is still dominated by hand stitching methods. A curved needle with a thread attached is typically held by forceps, with which a nurse forces the needle through the tissue on one side of a wound and, following the curve of the needle, across the opening and up through the tissue on the opposite side of the wound. The nurse releases the forceps' hold on the needle and with the forceps re-grasps a portion of the protruding needle. The needle is pulled through with the thread following along. The thread is manually drawn tight, knotted and cut. This process is repealed to form multiple stitches (stitch and suture are herein defined as equivalents) until the wound is closed.

Similarly, hand methods of ligating or tieing off anatomical vessels (e.g. blood arteries and veins, etc.) and ducts (e.g. bile ducts, etc.) still dominates this art. A previously knotted thread is passed over the end of a vessel, tightened to occlude the vessel, and the loose ends of the thread are snipped off. If the vessel or duct passes through the surgical site with no end present, the suture thread is passed around the vessel, knotted externally, tightened and the loose ends cut.

Although the forgoing process is easily accomplished on wounds in the skin with easy access and room to work, in areas of limited access the required manipulation of the forceps may be impossible. This is especially true of internal wounds, for example to internal organs, tendons, cartilage, etc. Here a large opening in the external skin, with the attendant trauma and morbidity, is made providing room to suture. In addition the knots of the tied sutures are irritants and may become lodged in the tissue creating difficult removal of the stitches.

Other limitation stem from the manual nature of the stitches. The force used, the depth of the stitch, the tautness of the resulting stitch and the knotting may vary significantly resulting in areas of infection, discomfort and scarring.

There have been attempts to improve suturing. U.S. Pat. No. 5,037,433 titled "Endoscopic Suturing Device and Related Method and Suture", issued to Peter J. Wilk et al. on Aug. 6, 1991 discloses one such attempt. Wilk et al. teach an elongated, flexible tube containing a smaller tube. This smaller tube contains a spring needle, forced straight while in the tube, but if unrestrained would form an arc shape. A thread is attached to the curved needle. The smaller tube is placed adjacent to the wound opening and the spring needle slides out from the smaller tube. The needle bends into the arc shape as it extends from the tube and so penetrated the tissue arcing down, across the wound opening and finally up on the opposite side of the wound where the needle protrudes. Through the outer flexible tube, an elongated forceps is inserted which grasps the protruding portion of the needle and pulls the needle through with the thread trailing. The thread is knotted completing the stitch. This device is designed for hard to reach areas where there is not enough room for manual suturing techniques. However the need to re-grasp the needle to complete the stitch, the difficulty of tieing remotely through the tube are limitations remaining with this device.

Other devices are known in the art wherein a suture or suture like needle is mechanically forced through tissue closing the wound.

Another device is described U.S. Pat. No. 3,638,653 titled "Suturing Device", issued to H. Lee Berry on Feb. 1, 1972, discloses a hollow suturing needle through which a thread is drawn.

These foregoing devices mechanically force the needle through the tissue and presumably do so in a consistent, repeatable manner, but the devices are cumbersome and most use the standard suture or a very similar needle. These device share common problems. The attachment of the needle to the thread and the ability to remove the needle while leaving the thread are common problems with these devices. The drawing, cutting and tieing of the thread remain to be done manually or with another instrument. The manual processes entail problems of tautness, knotting and other inconsistencies.

An object of this invention is to overcome the above illustrated limitations and problems by providing means; to perform suturing which penetrates tissue leaving a thread, to perform ligating which surrounds vessels or ducts with a thread, to draw the thread taut closing the wound or occluding the vessel, and then to cut and secure the thread in a reliable repeatable manner.

It is a another object to perform suturing with one device which completes the stitching in one operation.

It is a further object of this invention to complete the stitch without a knot. This removes an area of discomfort and difficulties if the knot becomes buried in the tissue, further to use materials which need not be removed but are absorbed by the host tissue.

It is yet another object of of this invention to provide an instrument well suited to perform suturing and ligating in areas of limited access, such as arthroscopic, laparoscopic and other endoscopic assisted procedures, wherein the suture is completed with a minor opening in the tissue as compared to opening usually associated with such procedures.

It is yet another object to limit the trauma and morbidity generally associated with internal suturing, by requiring only a small opening in the external tissue.

It is another object of the invention to provide a suturing device well suited to grafting, closing off blood vessels and other minimally invasive procedures.

Another object of this invention is the ability to introduce a gas into the opening which distends the cavity for visual inspection during endoscopic surgery, and to purge the joining area to ensure a reliable weld.

SUMMARY OF THE INVENTION

The foregoing objects are met in a new suturing and ligating structure (device) and process. This new structure utilizes, in a preferred embodiment, a needle that is constructed with a channel suitable for accommodating suture thread. Herein needle is defined as a device which establishes a channel through tissue or around vessels and ducts suitable for passing suture material, and suture material and thread are synonymous herein. In the preferred embodiments the channel may be a hollow needle or a U-shaped channel. For suturing the needle penetrates the tissue on one side of the wound traveling below the wound and emerges from the opposite side of the wound. For ligating the needle surrounds the vessel or duct, pincer-like. The needle may be constructed to draw the wound, vessel or duct together as the needle penetrates the tissue or surrounds the vessel or duct. Alternatively the wound, vessel or duct may be closed by tightening the thread. When the channel through the tissue or around the vessel or duct is established, suture material is threaded through the channel and secured. The needle is removed leaving the thread. The thread is drawn and secured at a given tension, cut and the ends welded together whereupon the device is removed. Alternatively the cutting may be done as a separate hand operation, say by scissors, after the device is removed.

The suturing objects are also met by puncturing said tissue wherein a passage is created through the tissue. Suture thread is passed through said passage, tightened and joined forming a completed suture. In an embodiment the suture material is joined to the puncturing needle and trails the needle as the needle passes through the tissue. When the needle leaves the tissue the suture material remains in the passage. The suture material, extending from each side of the wound, is tighten, cut and joined by welding. The passage is define as a way through the tissue without any needle or other artificial or foreign device remaining in the tissue.

In a preferred embodiment the device comprises two curved, opposed pincer-like needles. The needles penetrate the tissue on either side of the wound meeting within the tissue below the wound. In ligating the needles surround the vessel or duct with the needles meeting opposite the device. As the needles come together the wound, vessel or duct is closed. These needle are each formed with cross sections that have U-shaped channels, and when the needles meet a continuous U-shaped channel is provided through the tissue or around the vessel or duct. The suture material is threaded through the U-shaped channel and secured, allowing the needles to be removed. The suture material is drawn taut to a given tension, cut and ultrasonically welded. The device is removed leaving a completed stitch.

Other objects, features and advantages will be apparent from the following detailed description of preferred embodiments thereof taken in conjunction with the accompanying drawings in which:

BRIEF DESCRIPTION OF THE DRAWINGS

FIG. 10A–B is a cross section of the tip with a detail view of the welding.

DETAILED DESCRIPTION OF PREFERRED EMBODIMENTS

Figure 1A:
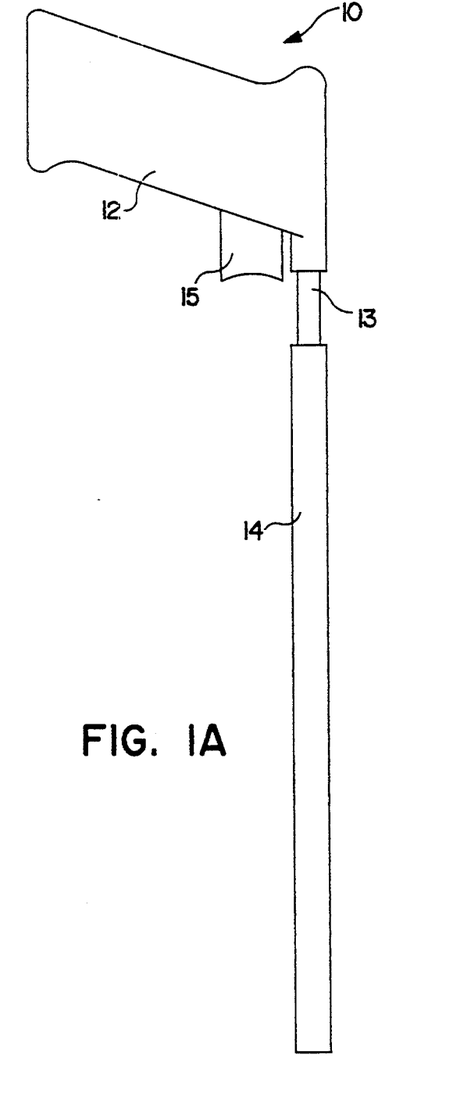
FIG. 1A is side view of the device, according to a first preferred embodiment of the invention.

FIG. 1A, shows a side view of a preferred embodiment 10 of the invention. A handle 12 houses a spool (not shown) of suture material, a battery, ultrasonic signal generating equipment and a controller. Alternatively an external housing electrically connected to the handle may contain a power supply, ultrasonic signal generating equipment and a controller.

Figure 1B:
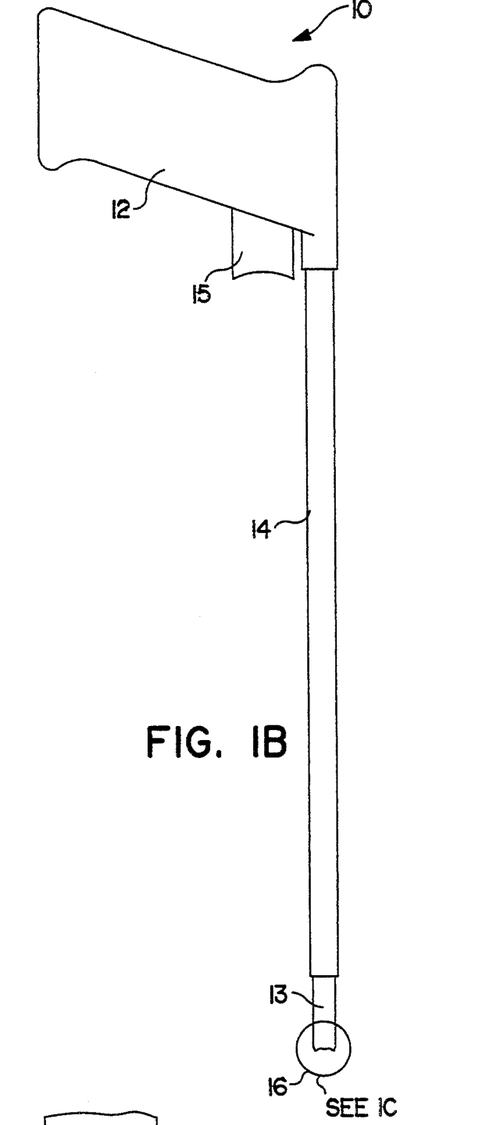
FIG. 1B is a side view of the device with the tip protective sheath retracted.
Figure 1C:
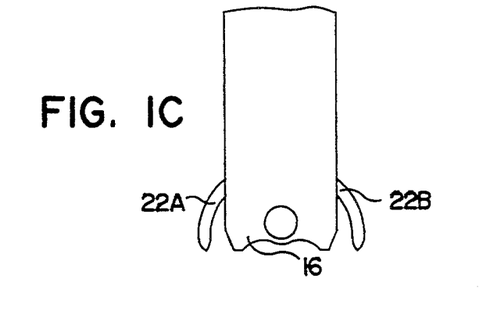
FIG. 1C is an exploded view detail of the tip of the (see FIG. 1B) device.

A shaft 13 extends from the handle 12, the shaft 13 is covered by a protective sheath 14 which is free to move axially along the shaft 13. FIG. 1B shows a side view of the device 10 with the protective sheath retracted exposing the tip 16 at the end of the shaft 13. The protective sheath 14 slides over protecting the tip 16 during handling and positioning of the device. The tip 16 is exposed when the device is in position and ready to create a stitch.

The handle 12 includes a multi-function trigger mechanism 15 which may, in other preferred embodiments, activate some of the processes described hereinafter. Alternative preferred embodiments include several triggers, switches and/or levers.

Another preferred embodiment (not shown) comprises a supply of gas, preferably carbon dioxide, communicating with the tip 16 through hollow passages, with a control valve at the handle, provides the gas to the tip 16. This arrangement allows, at the operator's option, a steady introduction of gas onto the area of surgery to distend the cavity for endoscopic viewing per current accepted surgical practice. When suturing the gas will maintain the weld area dry, or alternatively a burst of gas may be used to dry the weld area.

Figure 2:
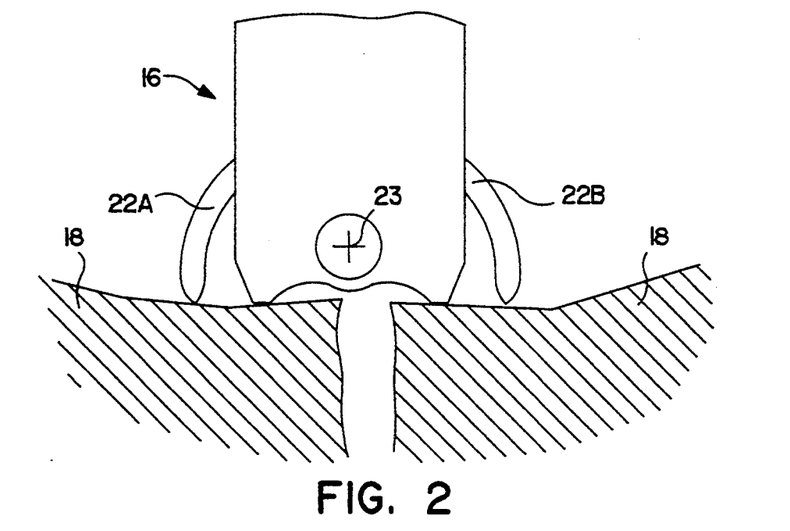
FIG. 2 is a side view of the tip of the device positioned over tissue (in section) straddling a wound to be closed.

FIG. 2 shows the tip 16 in contact with the tissue 18 straddling the wound 20 to be stitched closed.

Figure 3A:
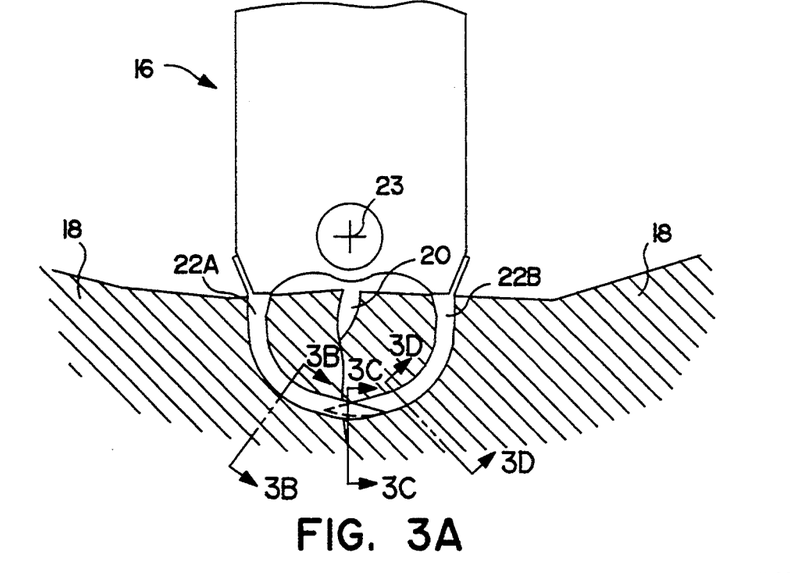
FIG. 3A is a side view of the tip with the channel established through the tissue (in section) with the wound partially drawn together.

Once the device is positioned straddling the wound, the left and right hand curved needles, 22A and 22B, respectively (collectively referred to as needles 22 below) are rotated about the pivot 23 penetrating the tissue 18, partially closing the wound 20, as in FIG. 3A. The needles 22 meet below the tissue surface and engage each other forming a continuous channel through the tissue traversing the wound 20.

Another preferred embodiment (not shown) comprises a single needle rotated through the tissue around the wound from one side.

Another preferred embodiment comprises a needle or dual needles utilizing a moving pivot.

Figure 3B:
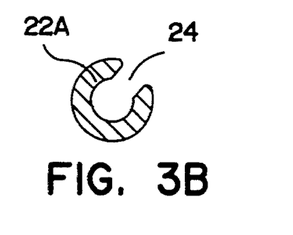
FIG. 3B is a cross section of the left hand needle.
Figure 3C:
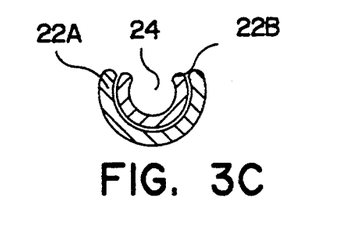
FIG. 3C is a cross section of the overlapping region of the left and right hand needles.
Figure 3D:
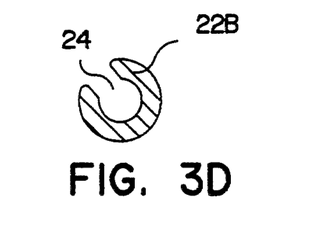
FIG. 3D is a cross section of the right hand needle.

FIG. 3B and FIG. 3D shows the cross section of each side of the needles 22, as the needles appear when inserted into the tissue. FIG. 3C shows the overlapping region of the needles 22 showing the right hand needle 22B nested inside the left hand needle 22A. As shown in the needles 22 form a continuous uninterrupted channel through the tissue, and this channel is sufficient for a suture thread to be inserted through the channel.

The needles are activated via linkages or a worm gear, joined to the proximate end of each needle, running down the shaft or by other known alternative mechanisms. Driving means, wherein said linkage is activated, drives said needles into the tissue.

Figure 4A:
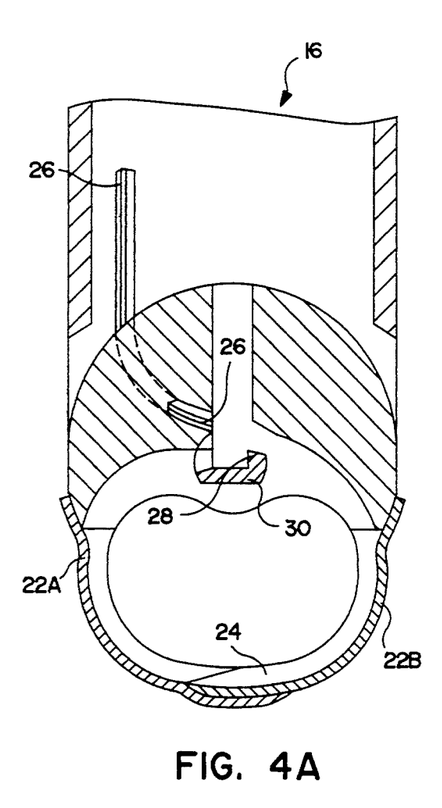
FIG. 4A is a section of the tip prior to threading the suture material through the channel.
Figure 4B:
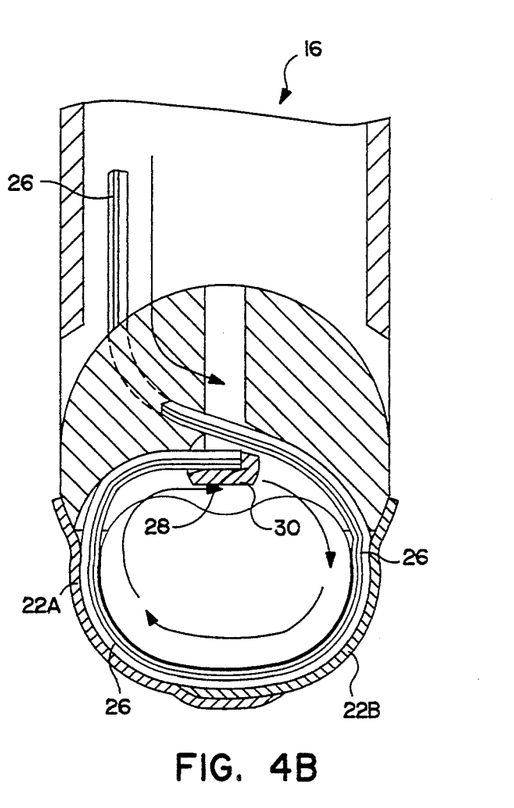
FIG. 4B is a section view of the tip prior to threading the suture material through the channel.

FIG. 4 shows the suture material threaded through the channel 24 until its path is blocked by a stop 28 on the weld anvil 30. In other preferred embodiments the exact length of thread is advanced eliminating the need of the stop 28. The threading mechanism, in the housing 12 or the shaft 13, is known in the art.

Figure 5A:
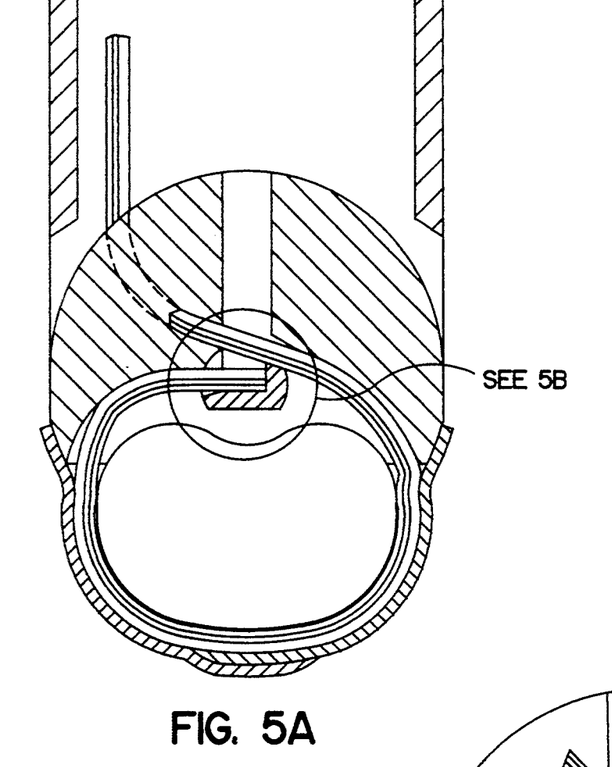
FIG. 5A is an isometric detail of the clamping and welding area in the tip of the device, showing the first clamp.
Figure 5B:
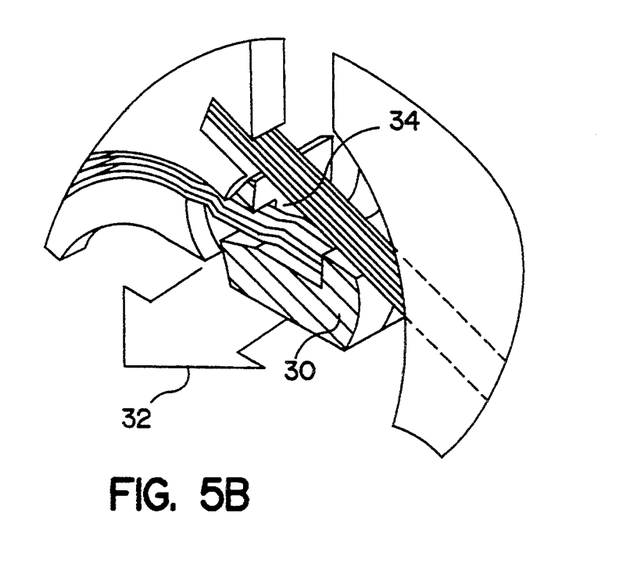
FIG. 5B is an exploded isometric view of the tip showing the motion and clamping action of the anvil.

In FIG. 5B the weld anvil moves in the direction of the arrow 32. A vertical extending member 34 of the anvil 30 is forced against the suture material 26, clamping and securing the material against a wall (not shown) of the tip 16 housing. In other preferred embodiments a vertical rod may be used to clamp the material 26 or forceps-like mechanism to grasp the material 26.

Figure 6:
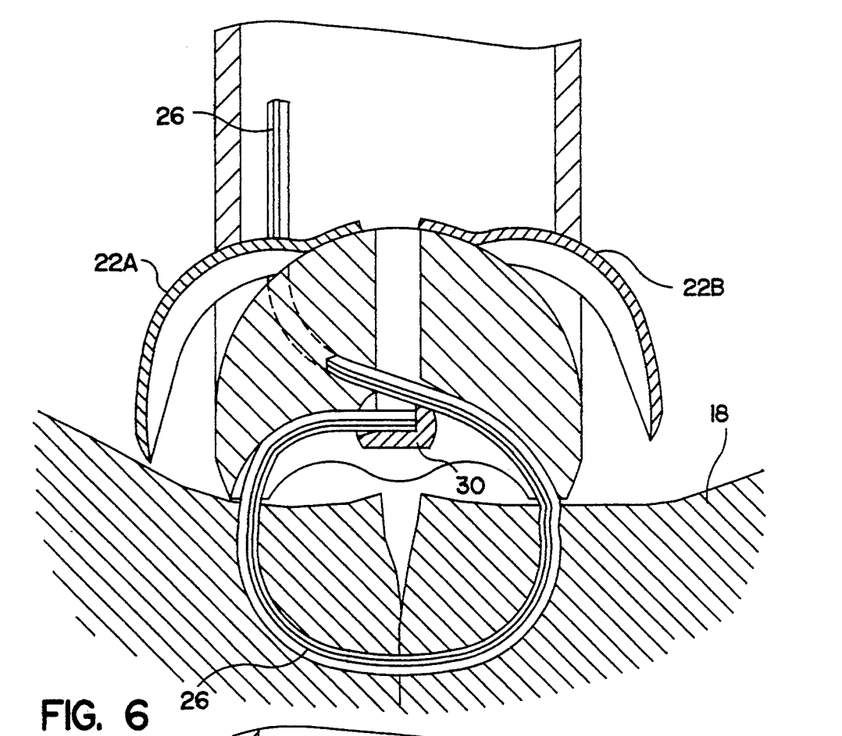
FIG. 6 is a cross section of the tip of the device after removing the needles with the suture material remaining.
Figure 7:
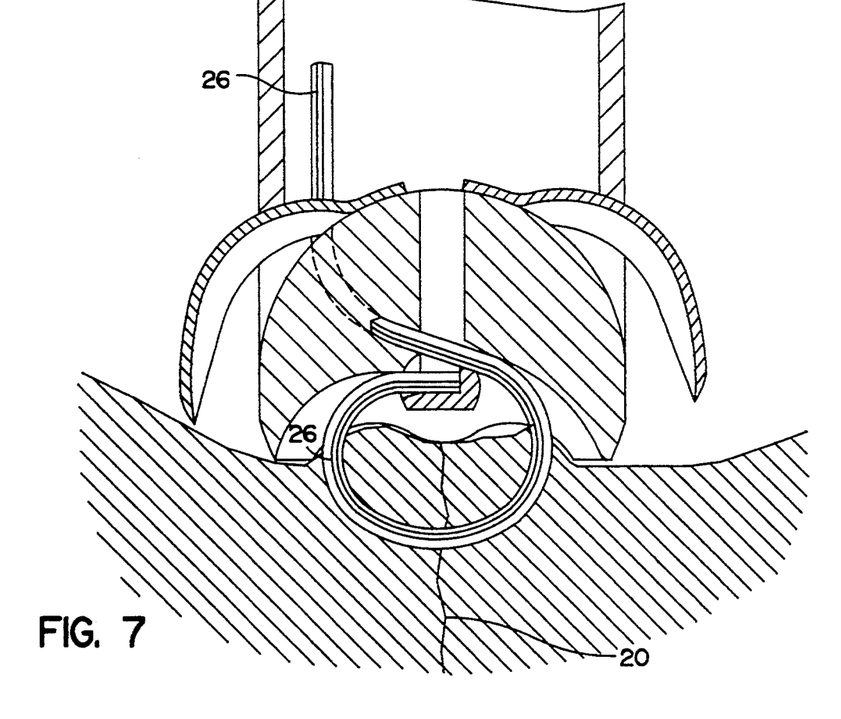
FIG. 7 is a cross section of the tip after drawing the thread taut.

FIG. 6 depicts the result after the needles 22 are withdrawn leaving the suture thread 26 through the tissue 18 secured at the anvil 30. FIG. 7 shows the thread 26 drawn taut until a desired tension is achieved thereby fully closing the wound 20. The material is tightened by a mechanism within the housing 12. Such a mechanism may be a drive system to rewind the spool or a mechanical collar to tighten onto the material and draw the material taut other such mechanisms are known in the art.

Figure 8A:
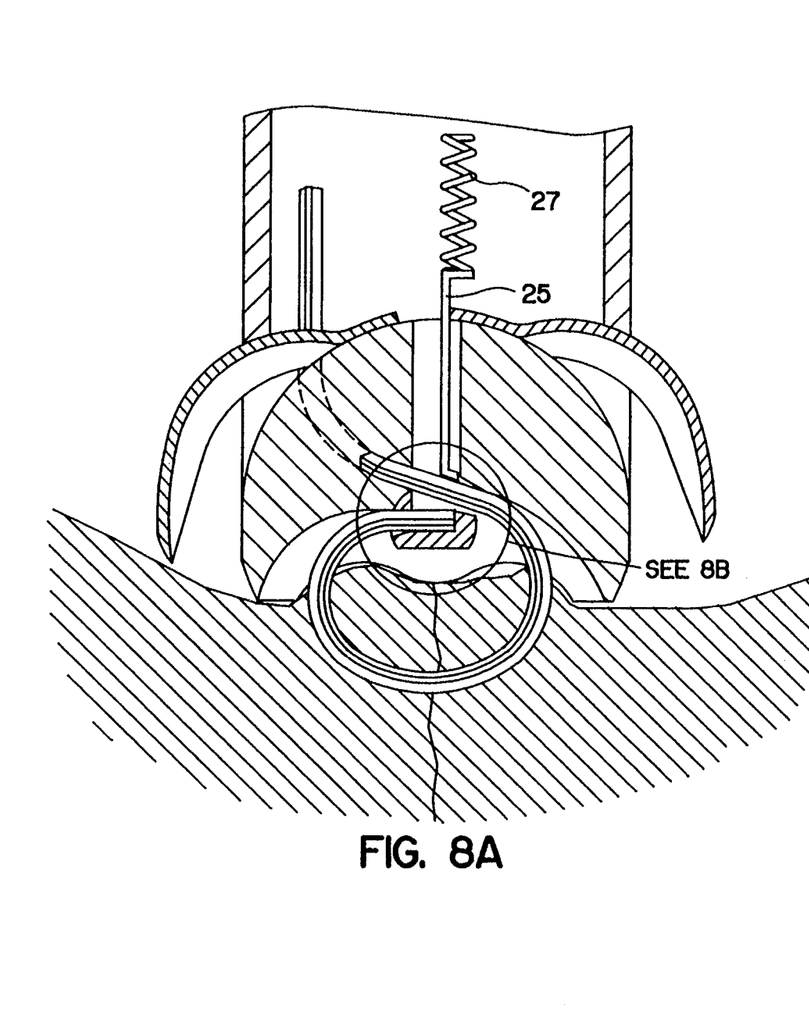
FIG. 8A is another cross section of the tip.
Figure 8B:
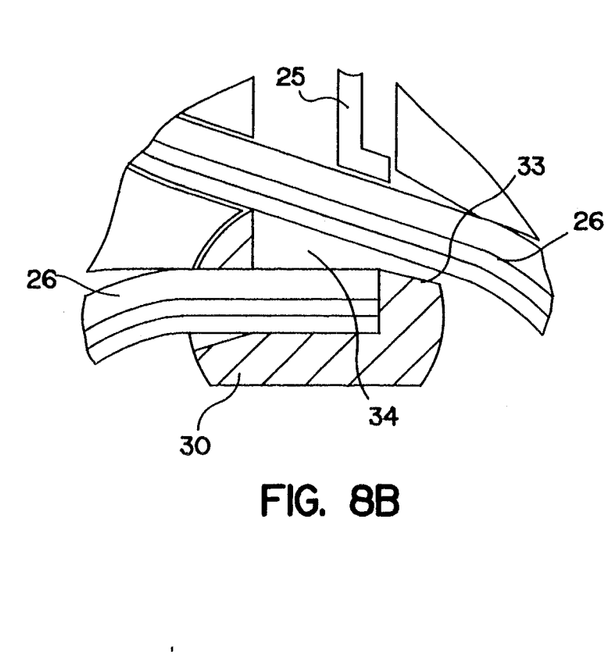
FIG. 8B is a cross section view of the second clamping device.

FIG. 8A shows a spring loaded clamp 25 which, when activated, forces the suture thread 26 against the anvil 30. FIG. 8B show in detail where the clamp 25 comes down firmly holding the suture material 26 against the anvil 30 surface 33. Operation of the clamp 25 is accomplished by linear advancement of the ultrasonic welding mechanism (not shown) to which the clamp 25 is attached via the spring 27. In another preferred embodiment the clamp 25 is activated by using known means, either manual or automatic via the controller. Still referring top FIG. 8B the needles 22 are withdrawn from the tissue, the suture material is taut and held at both ends with an overlap 34.

Figure 9A:
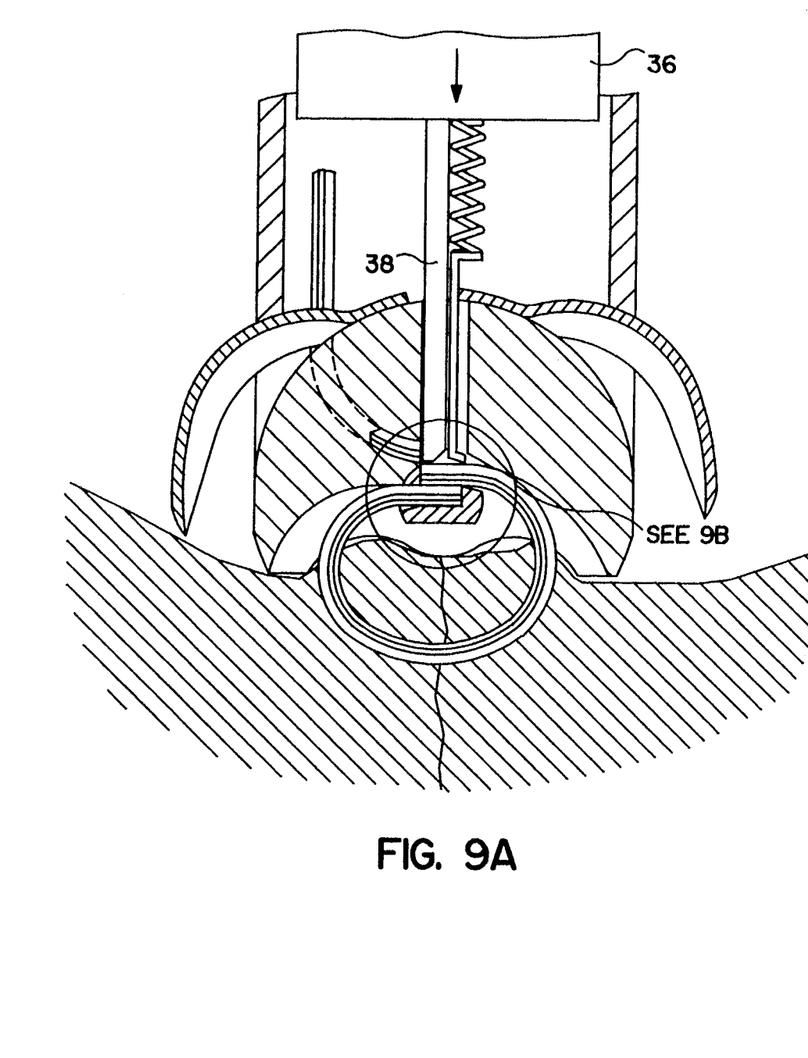
FIG. 9A is a cross section view of the tip.

FIG. 9A adds an ultrasonic welding mechanism. This mechanism has a piezoelectric stack 36 coupled with a tuned ultrasonic weld horn 38 extending towards the anvil 30.

Figure 9B:
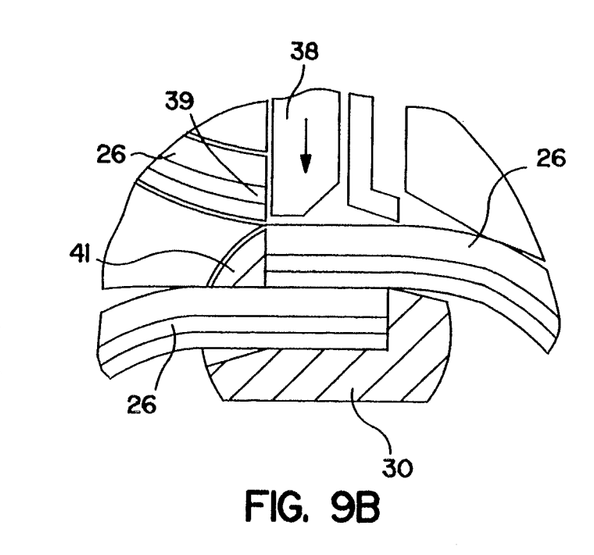
FIG. 9B is a cross section view of the cutting and welding mechanism.

The suture material is cut by advancing the horn 38 along the shaft 13 until the horn edge 39 shears the material against the sharp protrusion 41 on the anvil. Other manual or automatic shearing mechanisms known in the art may be alternatively used. Activation of the piezoelectric stack accomplishes the welding of the suture material, and the stack 38 may be activated before, after or during the advancement of the horn which cuts the material.

As shown in FIG. 10 the ultrasonically vibrating welding horn 38 continues advancing toward the tip 16 compressing the suture material 26 against the underlying suture material in the overlapping region 34. Ultrasonic energy transferred through the horn 38 melts the suture material 26 in the overlapping region 34. The controller, e.g. a microprocessor, a computer and program or the like, regulates the energy imparted to the suture material to produce an optimum weld characteristic. The piezoelectric stack is then deactivated. Other preferred embodiments employ magnetostrictive apparatuses or other known ultrasonic drivers in place of the piezoelectric stack as an ultrasonic energy source to cut and/or join (weld) the suture material. Still other preferred embodiments employ heating mechanisms such as resistance heating elements or laser sources in place of the ultrasonic welding mechanism to cut and join the ends of the suture material loop. The energy required to join the suture material ends and the time to permit resolidification of the molten suture material is well known in the art for different suture materials, e,g, polymer monofilament, and for the various threads sizes available. Both the horn 38, at the weld site, and the spring loaded clamp 25 stay in contact with the suture material maintaining the clamping action for a predetermined (known) time period allowing the molten suture material to re-solidify, thereby completing the weld.

This joining of the two ends of the suture material is completed with no loose ends extending from the weld area, so preventing snagging or similar disturbances of the stitch.

The horn 38, the vertical extending member 34 and the spring loaded clamp 25 stay in contact with the suture material for the known time period required for the molten material to re-solidify completing the stitch.

Figure 11A:
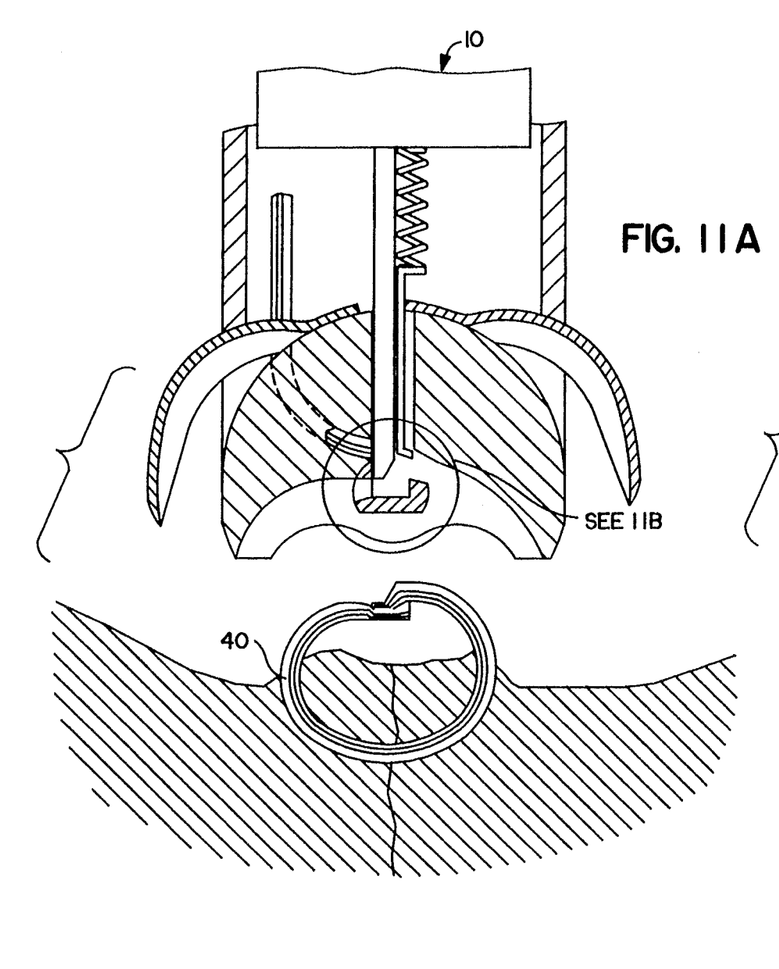
FIG. 11A is a cross section of the tip and the completed stitch (suture)
Figure 11B:
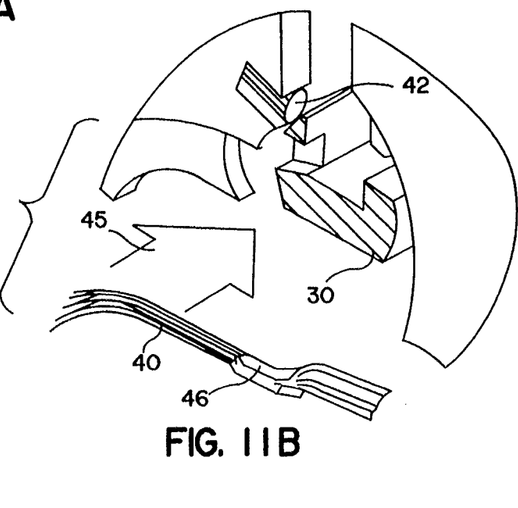
FIG. 11B is an exploded view of the tip shown in FIG. 11A.

FIG. 11A shows the weld anvil 30 being retracted (in the direction of the arrow in FIG. 11B) releasing the completed stitch. The device 10 may now be completely withdrawn. The blow up shown in FIG. 11B shows the cut suture end 42 ready to be threaded through the needles for the next stitch. The knotless weld 46 and the anvil 30 retracted in the direction of the arrow.

Figure 12:
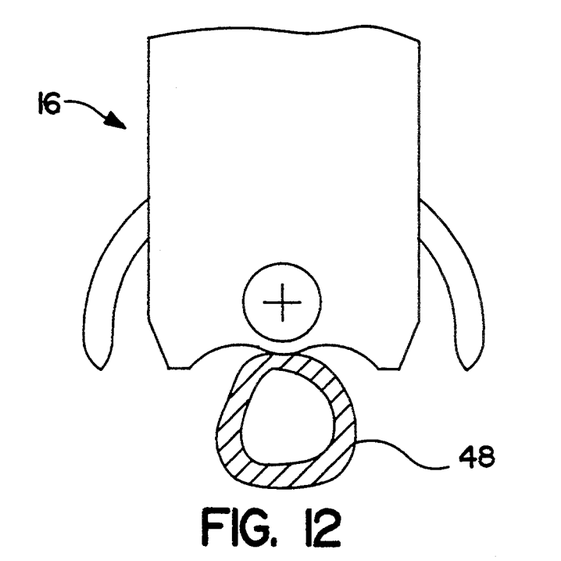
FIG. 12 is a side view of the tip of the device positioned proximate a vessel or duct (in section) to be ligated.
Figure 13:
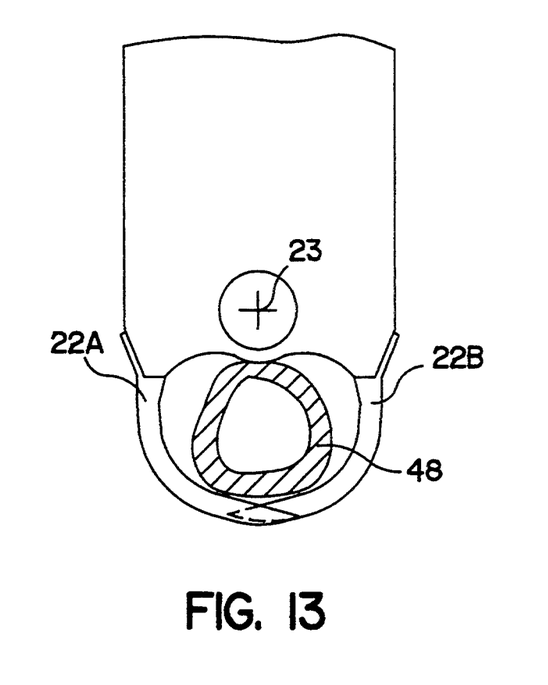
FIG. 13 is a side view of the tip with the channel established around the vessel or duct (in section)

The process for creating a ligating stitch to occlude a vessel or duct is identical to the process described above except that the passage and channel through which the thread is passed is created around the vessel or duct rather than through tissue. It should be noted that ligature could be used to advantage to secure tendons, ligaments and the like away from the surgical site of interest. FIG. 12 shows the tip 16 positioned proximate the vessel or duct 48 to be ligated. FIG. 13 shows the needles 22 rotated about the pivot 23 such that they engage, forming a continuous channel aroun the vessel or duct 48.

The suture thread is then advanced as shown in FIG. 4A and 4B.

The distal end of the thread is then clamped as shown in FIG. 5A and 5B.

Figure 14:
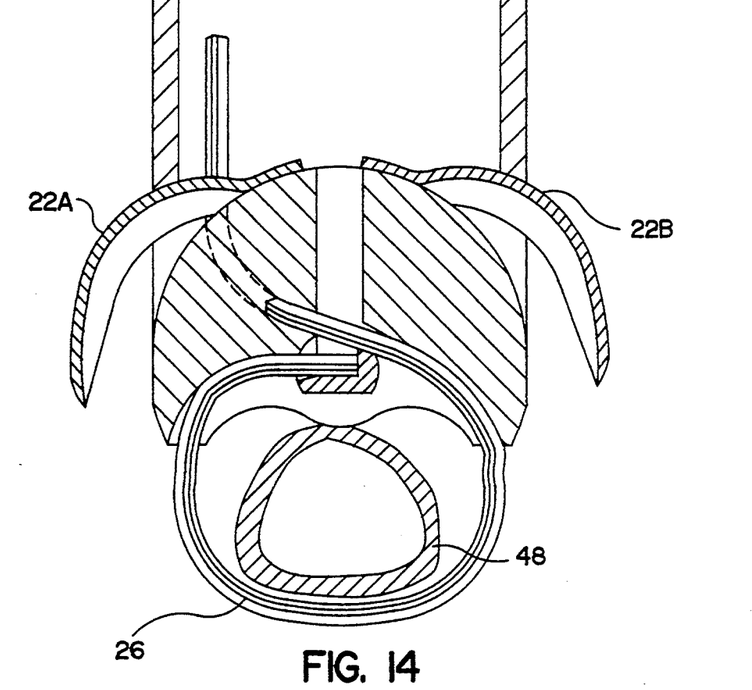
FIG. 14 is a cross section of the tip of the device after retracting the needles with suture thread remaining around the vessel (in section) to be ligated.

FIG. 14 shows the needles 22 retracted in the same manor as shown in FIG. 6, leaving a loop of suture thread 26 around the vessel or duct 48.

Figure 15:
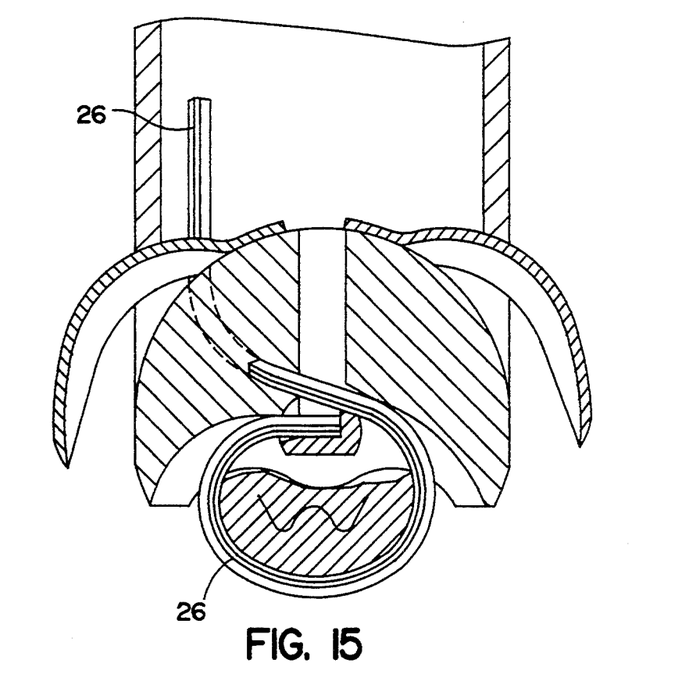
FIG. 15 is a cross section of the tip after drawing the thread taut to close the vessel to be ligated (in section)

The suture thread is then tightened as shown in FIG. 7. FIG. 15 shows the tightened suture thread occluding the vessel or duct 48 to be ligated.

Figure 10A:
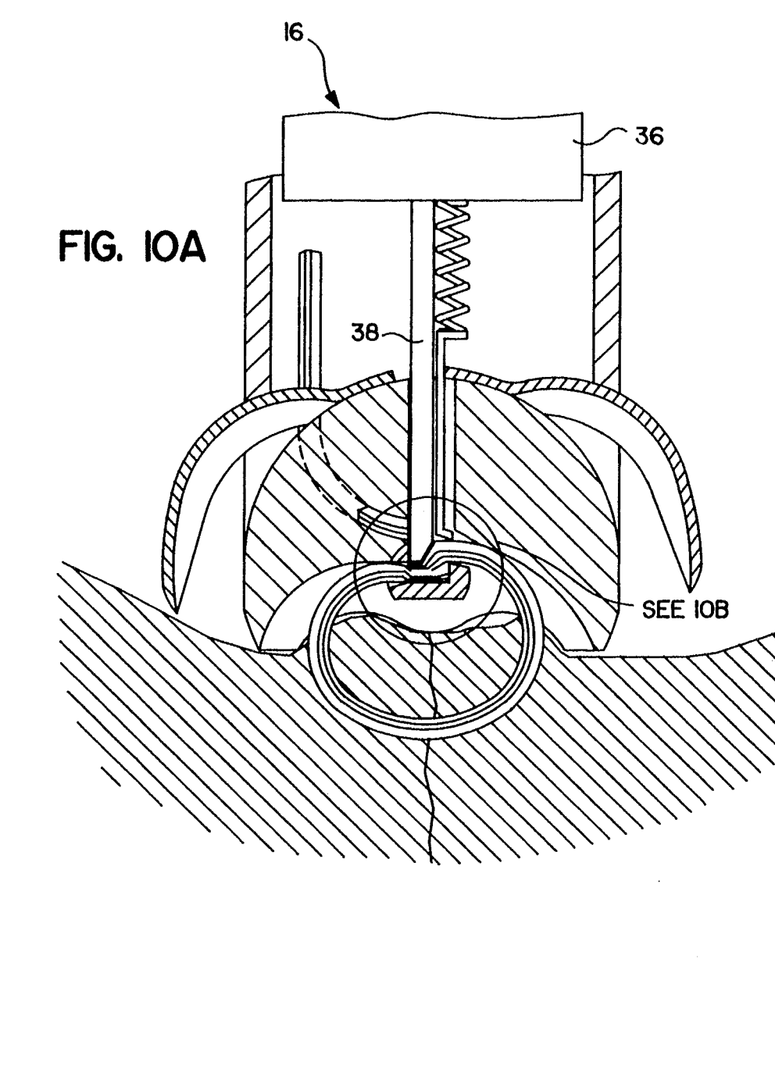
Figure 10B:
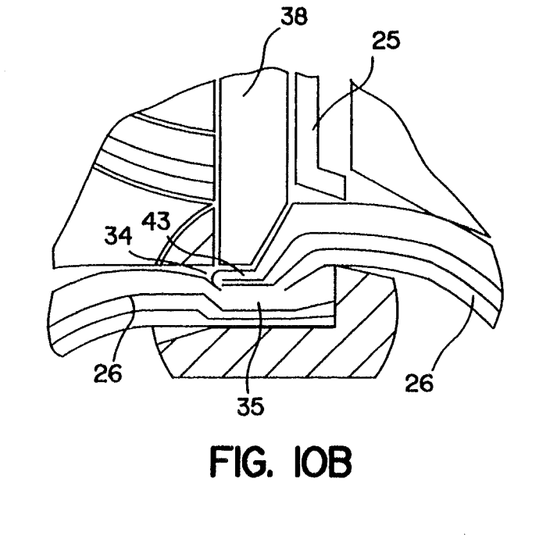

The proximate portion of the thread is then clamped as shown in FIG. 8A and 8B, cut as shown in FIG. 9A and 9B, and welded as shown in FIG. 10A and 10B.

Figure 16:
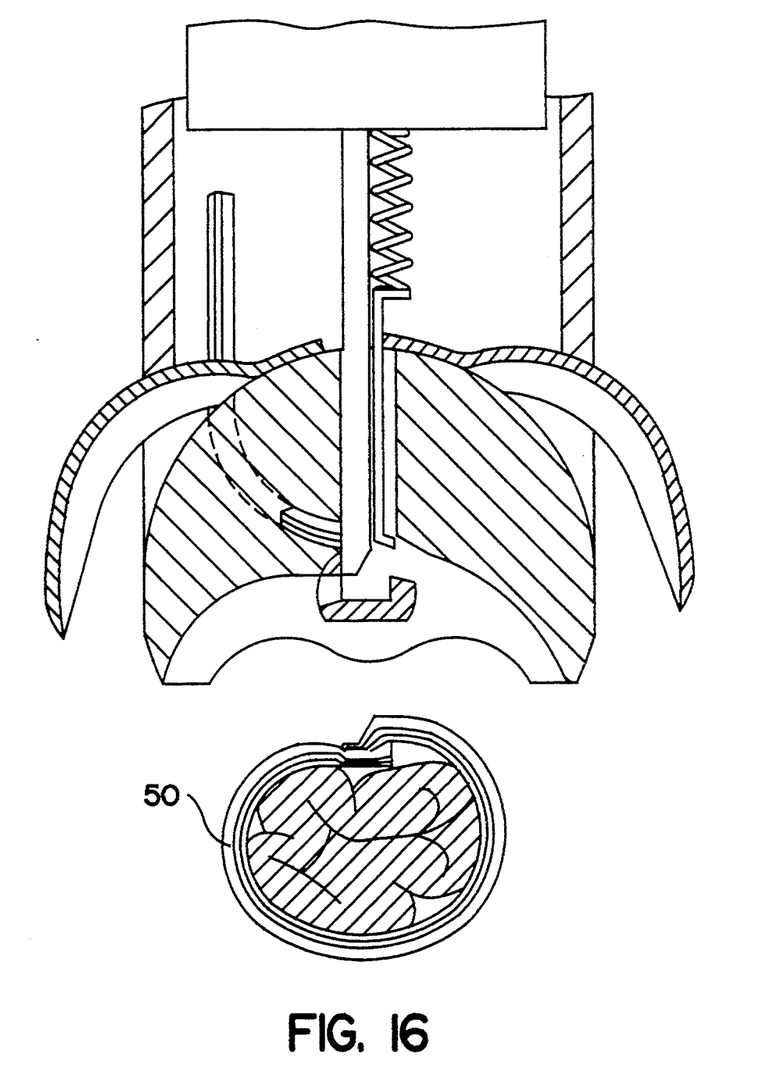
FIG. 16 is a cross section of the tip and the completed ligating stitch.

Finally, the completed ligating stitch released as shown in FIG. 11A and 11B. FIG. 16 shows the completed ligating stitch 50 and the occluded vessel or duct 48 (in section).

It will now be apparent to those skilled in the art that other embodiments, improvements, details and uses can be made consistent with the letter and spirit of the foregoing disclosure and within the scope of this patent, which is limited only by the following claims, construed in accordance with the patent law, including the doctrine of equivalents.

What is claimed is:

1. An automatic device for suturing tissue comprising, in combination:
    (a) a housing having proximal and distal ends, said distal end adapted to be placed adjacent to a suturing location,
    (b) means for puncturing said tissue, constructed at said distal end of said housing to form a passage through said tissue which suture thread is to be threaded, and where said passage communicates with at least one opening through said housing,
    (c) means for threading said suture thread, said threading means constructed on said housing where said suture thread is aligned with and proximate to said passage opening,
    (d) means for tightening said suture thread, said tightening means constructed on said housing and connected to the suture thread, external from the passage, for tightening the suture thread, and
    (e) means constructed on to the housing adjacent to said passage opening for welding to each other the entering and exiting portions of said suture thread at said passage opening, thereby creating a completed suture proximate said tissue.

2. A device as defined in claim 1 wherein said puncturing means comprises a needle constructed with a hollow or semi-enclosed cross section, said needle, when removably puncturing said tissue, forms said passage.

3. A device as defined in claim 2 wherein said puncturing means comprise two opposing, retractable, curved needles, rotatably mounted where said needles when activated puncture said tissue in a curved manner meeting within said tissue to form a continuous channel through said tissue.

4. A device as defined in claim 1, wherein said welding means comprise ultrasonic welding means.

5. A device as defined in claim 1, further comprising a microprocessor controller wherein said energy and time, introduced into said suture thread ends to be welded, are controlled by said microprocessor thereby producing a reliable, repeatable weld.

6. A device as defined in claim 1, further comprising a shaft with a first opening at the weld area and the shaft with a second opening distal from the weld area arranged and constructed to accept gas that travels through the shaft to dry the weld.

7. A device as defined in claim 1 further comprising means for cutting said suture thread, wherein said cutting means and said welding means are aligned such that said completed stitch has no loose ends.

8. A device as defined in claim 1 further comprising means for storing a continuous supply of suture thread wherein the thread storing means is arranged and constructed to feed the thread to said threading means immediately after a stitch is completed.

9. A device as defined in claim 1 wherein said device is constructed and arranged providing a long narrow shaft suitable for probing hard to reach and internal locations in humans and animals said puncturing means connected at the distal tip of the long shaft, and said threading, tightening and welding means running through said shaft to the tip.

10. A device as defined in claim 9 wherein said long narrow shaft is articulated.

11. An device as defined in claim 1 wherein said suturing device forms a completed suture without repositioning said device.

12. An automatic suturing and ligating device comprising:
    (a) housing means,
    (b) tubular means fixed within and extending from said housing ending with a tip, wherein said tip contacts tissue where a suture is to be placed or a vessel where a ligature is to be placed,
    (c) tubular sheath means slidably fixed and covering said tip thereby protecting said tip from damage,
    (d) the tip including dual, opposing curved needles having U-shaped channels in each needle, said channels running the length of the curved needle, and where said needles are positioned on either side of an opening in said tissue or astride said vessel,
    (e) linkage movably fixed within said tube means, joined to the proximate end of each needle,
    (f) drive means connected to said linkage wherein said linkage is activated and drives said needles into the tissue or around said vessel, wherein said needles penetrate the tissue in a curving manner or surround said vessel, and wherein said needle points meet thereby forming a channel,
    (g) a supply of suturing thread, fixed within said housing, wherein said thread extends through said tube means to the tip, and where said thread is positioned to be threaded through the channel,
    (h) thread drive means which forces the thread through the channel wherein said thread forms a completed loop, said thread drive means fixed within said housing and constructed and arranged to accept and contact said thread and guide said thread to and through said channel, (i) an anvil, fixed within said tip, and releasably arranged within said loop such that the suture threads overlap one side of said anvil with the tissue on the other side of said anvil, (j) a clamping member, movably fixed to and extending through said tube means, arranged to contact the anvil with the suture thread therebetween, securing said threads to said anvil such that said needles can be extracted from the tissue leaving the suture thread in place, (k) a mechanical assembly fixed to said housing and grasping said thread, and activation means for said assembly wherein said assembly when activated draws said thread and tightens the loop thereby closing said tissue opening, (l) tension controlling means connected to said mechanical assembly and arranged and constructed to measure the tension in the suture thread wherein said activation means draws said thread tight until said tension equals a preset level, (m) a second clamping member movably fixed to and extending through said tube means which when activated clamps said thread loop, where the two threads on either side of said loop overlap, such that both threads are secured by said second clamp, (n) a welding horn fixed within said tip and constructed and arranged for compressing said suture material at said overlap area between said clamping means, (o) an edge means interferently fixed adjacent to the path of said second clamping member wherein said welding horn strikes the edge means with the suture thread therebetween and shears off said thread from said spool, (p) a drying gas supply and regulating means fed through said tube means and positioned adjacent and drying said overlap region, (q) an ultrasonic generator connected to the welding horn and means to transfer said energy down said welding horn into said suture threads at the overlap, such that when activated said energy welds said threads together, proximate said tissue, thereby forming a closed loop stitch, and (r) computer and programming means arranged and constructed to connect to and control: said power (energy per unit time) into said suture threads whereby reliable welds are made, and said clamping members such that said suture thread is held until said weld has solidified, and (t) means for releasing connected to said anvil said suturing and ligating device whereby said anvil is retracted, freeing said closed loop stitch from said suturing and ligating device.

13. A method for suturing an opening in tissue comprising the steps of:

simultaneously puncturing said tissue from each side of said opening, said puncturing forming a passage through said tissue through which suture thread is to be threaded, threading said suture thread through said passage in said tissue, tightening said suture thread, and welding the portions of said suture thread that emerge from said tissue to each other proximate said tissue, thereby creating a completed suture where said welding step includes controlling the energy introduced into said suture material therein producing a reliable, repeatable weld.

14. A method for ligating a vessel comprising the steps of:

simultaneously surrounding said vessel from each side of said vessel forming a passage around said vessel through which suture thread is to be threaded, threading said suture thread through said passage, tightening said suture thread, and welding the portions of said suture thread that emerge from said tissue to each other, thereby creating a completed ligature, where said welding step includes controlling the energy introduced into said suture material therein producing a reliable, repeatable weld.

15. An automatic ligating device for vessels comprising, in combination:

(a) a housing with a distal end adapted to be placed adjacent to where a ligature is to be placed around said vessel, (b) means for surrounding said vessel constructed at said distal end of said housing and having a passage therethrough in which said ligature thread is to be threaded, and where said passage communicated with at least one opening through said housing, (c) means for threading said ligature thread, said means for threading constructed on said housing where said ligature thread is aligned with and proximate to said passage opening, (d) means for tightening said ligature thread, said tightening means constructed on said housing and connected to said ligature thread, external from the passage, for tightening said ligature thread, and (e) means constructed on the housing adjacent to said passage opening for welding to each other the entering and exiting portions of said ligature thread at said passage opening, thereby creating a completed ligature proximate said tissue.

16. A device as defined in claim 15 wherein said surrounding means comprises a needle constructed with a hollow or semi-enclosed cross section, said needle, when surrounding said vessel, forms said passages.

17. A device as defined in claim 16 wherein said surrounding means comprise two opposing, retractable, curved needles, rotatably mounted where said needles when activated surround in a curved manner the vessel to form a continuous channel.

18. A device as defined in claim 15, wherein said welding means comprises ultrasonic welding means.

19. A device as defined in claim 15, further comprising a microprocessor controller wherein said energy and time, introduced into said suture thread ends to be welded, are controlled by said microprocessor thereby producing a reliable, repeatable weld.

20. A device as defined in claim 15, further comprising a shaft with a first opening at the weld area and the shaft with a second opening distal from the weld area arranged and constructed to accept gas that travels through the shaft to dry the weld.

21. A device as defined in claim 15 further comprising means for cutting said suture thread wherein said cutting means and said welding means are aligned such that said completed stitch has no loose ends.

22. A device as defined in claim 15 further comprising means for storing a continuous supply of suture thread wherein the thread storing means is arranged and constructed to feed the, thread to said threading means immediately after a stitch is completed.

23. A device as defined in claim 15 wherein said device is constructed and arranged providing a long narrow shaft suitable for probing hard to reach and internal locations in humans and animals said puncturing means connected at the distal tip of the long shaft, and said threading, tightening and welding means running through said shaft to the tip.

24. A device as defined in claim 15 wherein said long narrow shaft is articulated.

25. An device as defined in claim 15 wherein said ligating device forms a completed ligature without repositioning said device.

* * * * *